US00PP24416P3

(12) United States Plant Patent
Madsen

(10) Patent No.: US PP24,416 P3
(45) Date of Patent: Apr. 29, 2014

(54) ***CAMPANULA* PLANT NAMED 'PKMM03'**

(50) Latin Name: *Campanula medium*
Varietal Denomination: PKMM03

(75) Inventor: Christian Hald Madsen, Korsor (DK)

(73) Assignee: Gartneriet PKM A/S, Odense N (DK)

( * ) Notice: Subject to any disclaimer, the term of this patent is extended or adjusted under 35 U.S.C. 154(b) by 142 days.

(21) Appl. No.: 13/506,398

(22) Filed: Apr. 17, 2012

(65) Prior Publication Data

US 2013/0276197 P1 Oct. 17, 2013

(51) Int. Cl.
*A01H 5/00* (2006.01)

(52) U.S. Cl.
USPC ..... Plt./414

(58) Field of Classification Search
USPC ..... Plt./414
See application file for complete search history.

(56) References Cited

U.S. PATENT DOCUMENTS

PP20,821 P2 * 3/2010 Pedersen ..... Plt./414

OTHER PUBLICATIONS

UPOV PLUTO QZ Citation for 'PKMM03' Jun. 15, 2012.*
UPOV PLUTO CA Citation for 'PKMM03' Apr. 30, 2012.*

* cited by examiner

*Primary Examiner* — Wendy C Haas
(74) *Attorney, Agent, or Firm* — Foley & Lardner LLP

(57) ABSTRACT

A new and distinct cultivar of *Campanula* plant named 'PKMM03', characterized by its upright, compact plant habit; dense and bushy plant form, mainly due to short, upright and stiff stems; vigorous growth habit, with no need for chemical growth retardation; higher number of flowers per plant; many cuttings on each stock plant; no need for vernalization for flower induction; and violet colored flowers.

6 Drawing Sheets

Latin name of genus and species of the plant claimed: *Campanula medium.*

Variety denomination: 'PKMM03'.

BACKGROUND OF THE INVENTION

The present invention relates to a new and distinct cultivar of *Campanula* plant, botanically known as *Campanula medium*, commonly known as Canterbury Bells, and hereinafter referred to by the name 'PKMM03'.

The new *Campanula*, 'PKMM03', is a product of a planned breeding program conducted by the inventor, Christian Hald Madsen, in Søhus, Denmark. The objective of the breeding program is to develop a new *Campanula* cultivar with upright, compact plant form and unique colored flowers.

The new *Campanula* cultivar originated from a cross made in a controlled breeding program by the inventor in 2011 in Søhus, Denmark. The female or seed parent is a cultivar from the proprietary breeding line of *Campanula medium* designated 45.11.1422 clone 17 (unpatented). The male or pollen parent is a cultivar from the proprietary breeding line of *Campanula medium* designated 45.07.0908BY (unpatented). The new *Campanula* 'PKMM03' was discovered and selected by the inventor as a single flowering plant within the progeny of the stated cross in April 2011 in a controlled environment in Søhus, Denmark. The inventor selected 'PKMM03' on the basis of its upright, compact plant habit, plant height, violet flowers.

Asexual reproduction of the new *Campanula* cultivar by terminal cuttings was first performed in April 2011 in Søhus, Denmark, and has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'PKMM03'. These characteristics in combination distinguish 'PKMM03' as a new and distinct cultivar:

1. Upright, compact plant habit;
2. Dense and bushy plant form, mainly due to short, upright and stiff stems;
3. Vigorous growth habit, with no need for chemical growth retardation;
4. Many cuttings on each stock plant;
5. No need for vernalization for flower induction; and
6. Violet colored flowers.

Plants of the instant cultivar 'PKMM03' differ primarily from plants of the parental cultivars, in the following characteristics:

1. Colour—female pink—offspring purple
2. Compactness—male vigorous—offspring compact Side-by-side comparisons were conducted by the inventor in Søhus, Denmark, among plants of the instant cultivar 'PKMM03' and plants of the most similar commercial cultivar, the *Campanula medium* designated 'PKMM01' (patented, U.S. Plant Pat. No. 20,910). Plants of the new *Campanula medium* 'PKMM03' differ from plants of *Campanula medium* 'PKMM01', primarily in the following characteristic:

1. Plants of the 'PKMM03' have violet petals whereas plants of 'PKMm01' have purple petals.

2. Plants of 'PKMM03' have a smaller number of lateral branches than 'PKMM01.
3. Plants of 'PKMM03' have a smaller number of flowers and buds per plant.
4. Plants of 'PKMM03' have longer leaf length than plants of PKMM01.

BRIEF DESCRIPTION OF THE PHOTOGRAPHS

The accompanying colored photographs illustrate the overall appearance of the new *Campanula* 'PKMM03', showing the colors as true as it is reasonably possible to obtain in colored reproductions of this type. Colors in the photographs may differ slightly from the color values cited in the detailed botanical description, which more accurately describe the actual colors of 'PKMM03'.

DETAILED BOTANICAL DESCRIPTION

Figure 1:
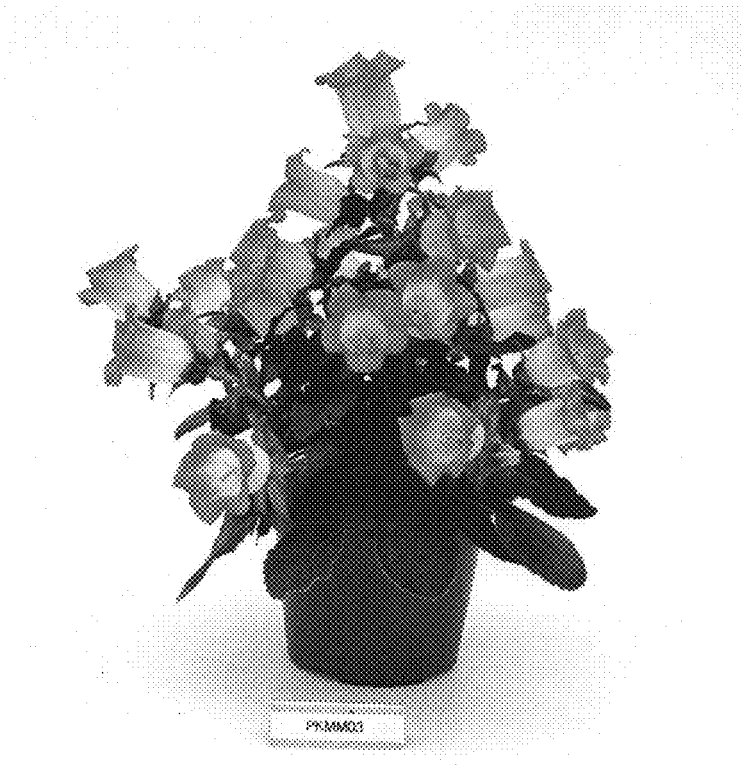
FIG. 1 shows a side perspective view of a typical flowering plant of 'PKMM03', as grown in a 10.5 cm pot at 11 weeks of age.
Figure 2:
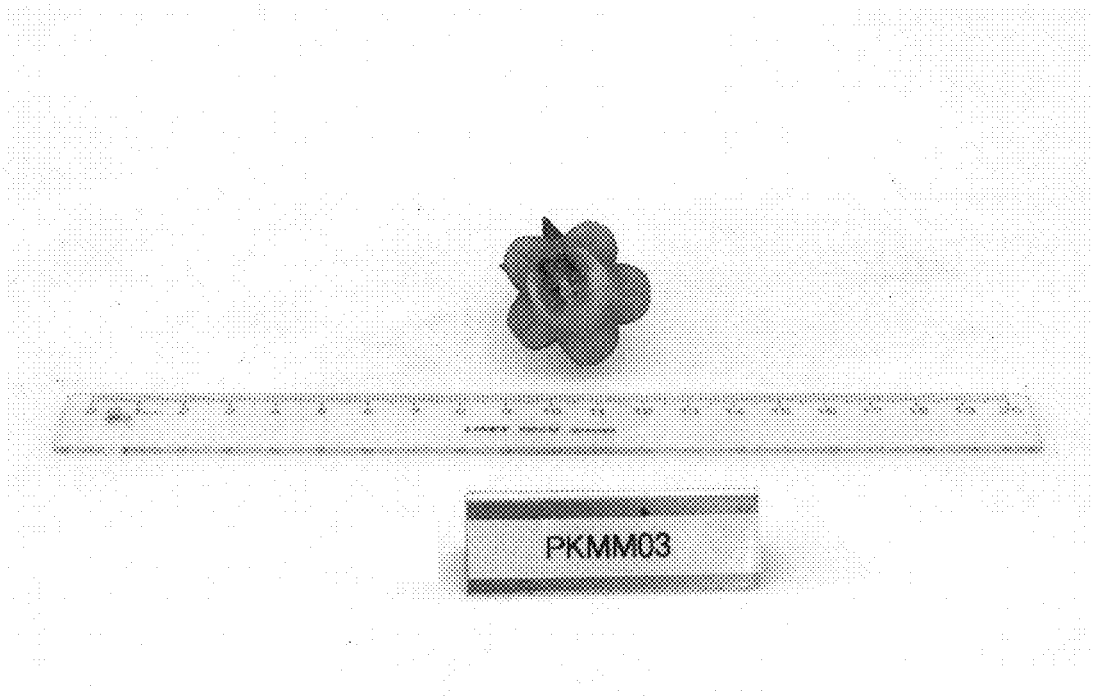
FIG. 2 shows a close-up top view perspective of a typical mature flower produced by 'PKMM03' at 11 weeks of age.
Figure 3:
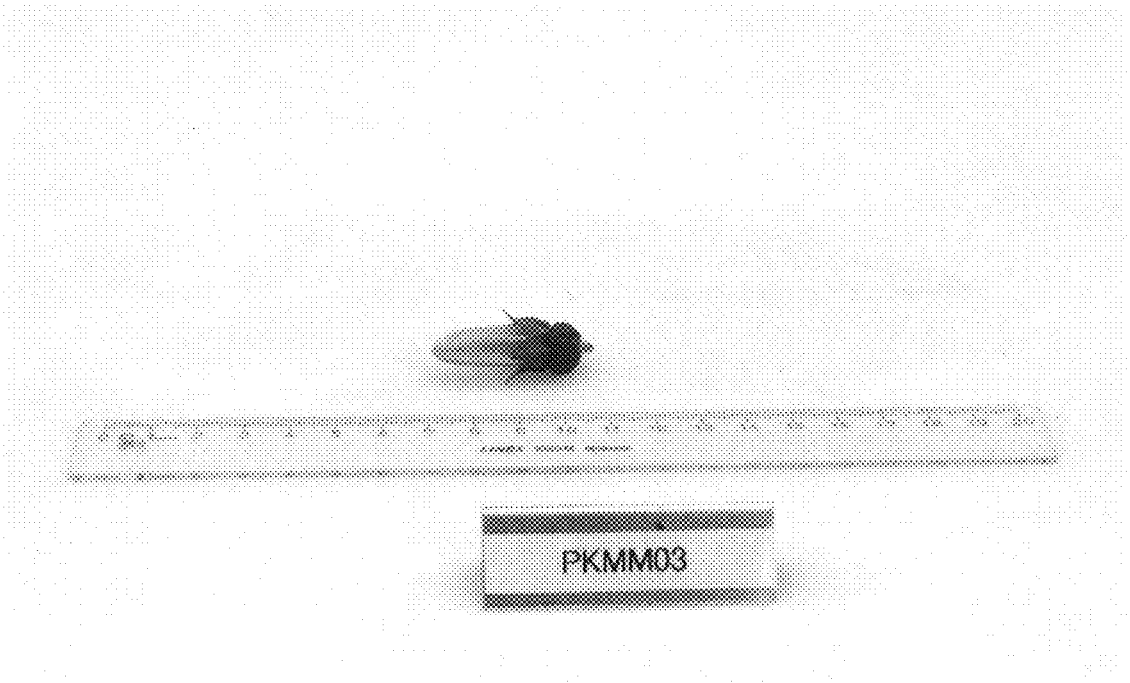
FIG. 3 shows a close-up side perspective view of a typical bud produced by 'PKMM03' at 11 weeks of age.
Figure 4:
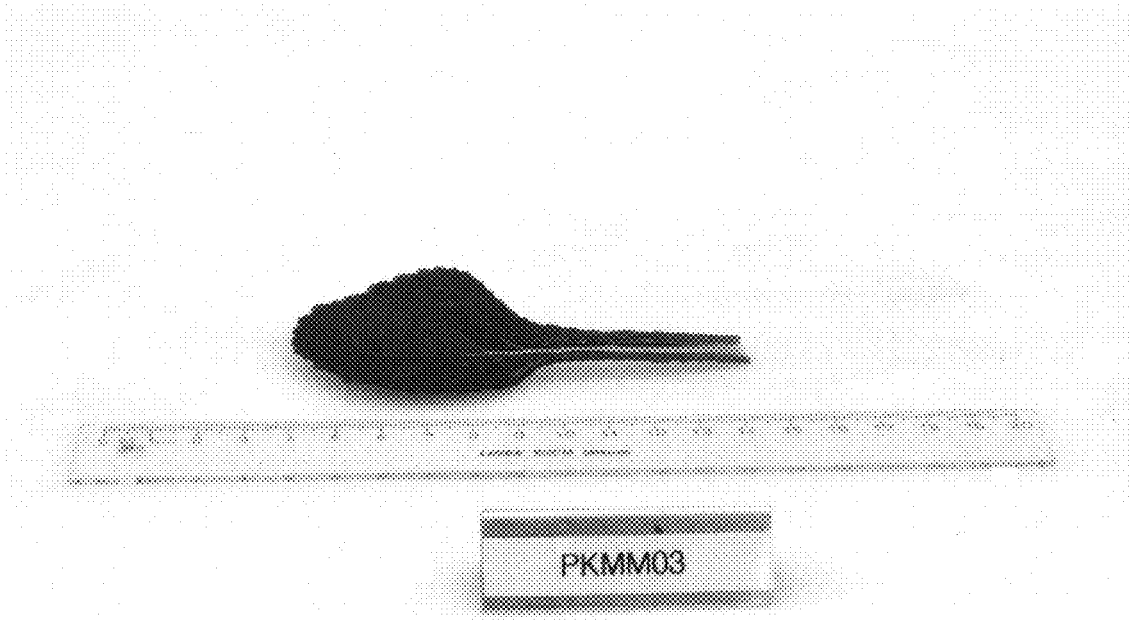
FIG. 4 shows a close-up view perspective of the upper surface of a typical basal leaf, produced by 'PKMM03' at 11 weeks of age.
Figure 5:
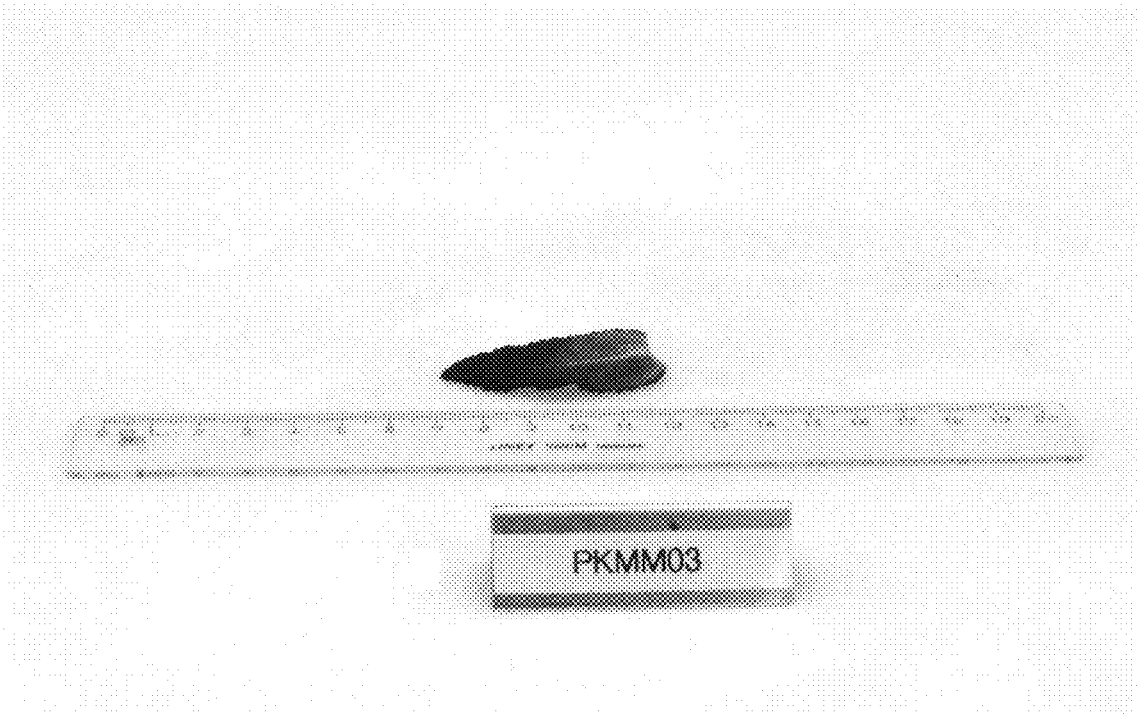
FIG. 5 shows a close-up view perspective of the upper surface of a typical apical leaf, produced by 'PKMM03' at 11 weeks of age.
Figure 6:
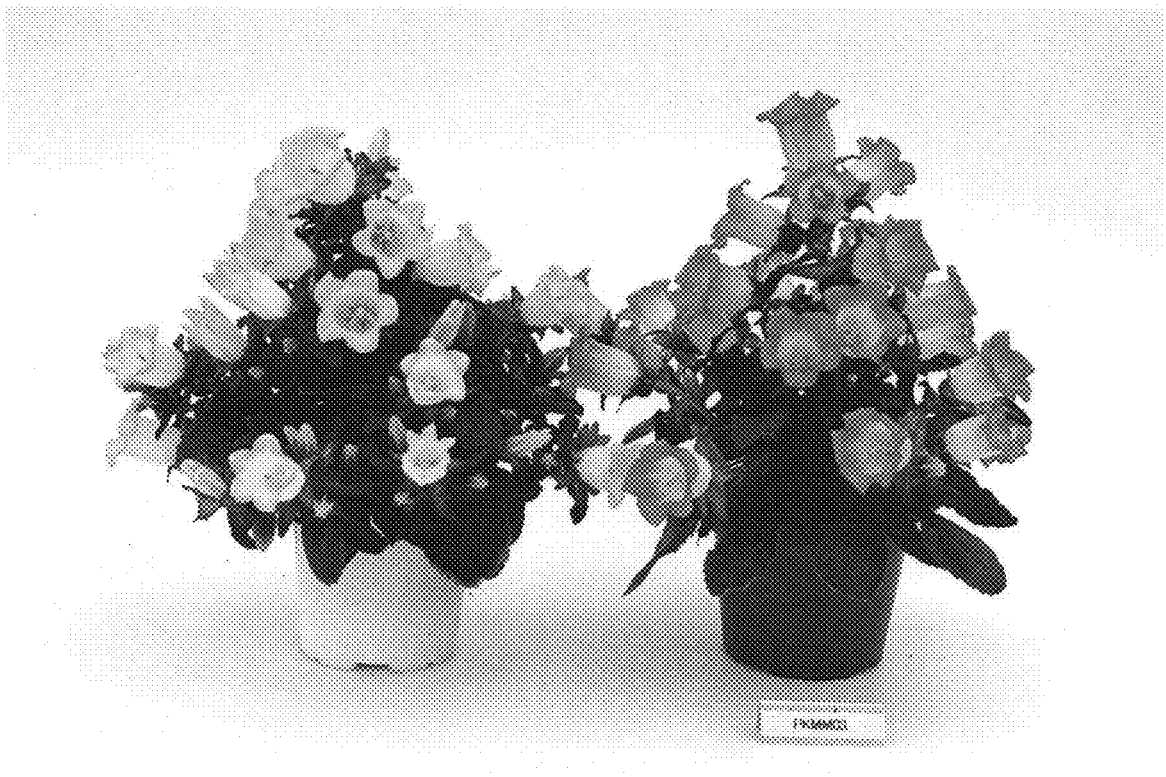
FIG. 6 shows a side perspective view of a typical flowering plant of 'PKMM03' compared with a typical flowering plant of 'PKMM01'.

The new *Campanula* 'PKMM03' has not been observed under all possible environmental conditions. The phenotype of the new cultivar may vary with variations in environment such as temperature, light intensity, day length, and fertility level without any variance in genotype.

The aforementioned photographs, together with the following observations, measurements and values describe plants of the new *Campanula* 'PKMM03' as grown in a heated and lighted, glass-covered greenhouse in Søhus, Denmark, under conditions which closely approximate those generally used in commercial practice where day and night temperatures in the greenhouse range from 18-22° C. Ambient light levels used while growing plants of 'PKMM03' are +100 $Wm^2$. Plants of 'PKMM03' are grown with 18 hour long day photoperiodic treatments from the third week. Propagation and young plants are exposed to 10 hour short photoperiodic treatments. No growth retardants used.

The age of the 'PKMM03' plants described is 11 weeks old and grown in 10.5 cm pots. The photographs and descriptions were taken during January 2011. Color references are made to The Royal Horticultural Society Colour Chart (R.H.S.), $5^{th}$ edition, except where general colors of ordinary significance are used.

Classification:

*Botanical.*—*Campanula medium.*

Parentage:

*Female or seed parent.*—Unpatented cultivar from the proprietary breeding line of *Campanula medium* designated 45.09.1180 clone 17 (unpatented).

*Male or pollen parent.*—Unpatented cultivar from the proprietary breeding line of *Campanula medium* designated 45.07.0908BY (unpatented).

Propagation:

*Type cutting.*—Terminal vegetative cuttings.

*Time to initiate roots.*—About 12 to 15 days at 18 to 21° C. in tunnels in a greenhouse.

*Root description.*—Fine, well branched, fibrous.

Plant description:

*Form.*—Annual, herbaceous plant with upright, compact plant habit. Produced as potted plant. Campanulate flowers in racemes. Freely branching with lateral branches forming at every node.

*Crop time.*—After rooting, about 11 weeks are required to produce finished flowering plants in 10.5 cm pots.

*Vigor.*—Vigorous growth rate.

*Plant height* (*from pot rim to top of plant plane*).—About 18 cm to 22 cm.

*Plant spread* (*width*).—About 23 cm to 26 cm.

*Lateral branches.*—Habit: Basal spreading branches and central upright stem when flowering. Quantity: About 10 to 13 per plant. Leaves per Lateral Branch: About 4 to 8. Length (including flowers): 9 cm to 15 cm. Diameter: About 2 mm. Internode Length: 7-15 mm.

*Stem.*—Shape: Round. Strength: Strong. Aspect: Upright and spreading. Texture: Pubescent. Color: RHS 145A — Yellow-green.

Foliage description:

*Basal leaves.*—Arrangement: Single. Overall shape: Elliptical. Apex shape: Rounded. Base shape: Cordate to truncate. Length: About 7 cm to 11 cm. Width: About 3 cm to 6 cm. Margin: Crenate. Texture (both sides): Velvety. Pubescence: Very short, stiff hairs on both sides, hispidulous.

*Apical* (*stem*) *leaves.*—Arrangement: Single, alternate. Overall shape: Oblong, elliptical. Apex shape: Acute. Base shape: Rosulate. Length: About 3 cm to 5 cm. Width: About 8-15 mm. Margin: Crenate. Texture (both sides): Velvety. Pubescence: Very short, stiff hairs on both sides, hispidulous.

*Basal & apical leaves.*—Mature: Upper surface: Green, RHS 137A. Lower Surface: Green, RHS 137A. Immature: Upper surface: Green, RHS 137C. Lower Surface: Green, RHS 137C. Venation: Pattern: Reticulate. Color (upper and lower surface): Young leaf: Green 137C. Mature leaf: Green 137A. Petiole: Basal Length: About 3 cm to 4 cm. Apical Length: Up to 1 cm. Diameter: 1.0 mm to 3.0 mm. Color: RHS 137A, green. Texture: Slightly Pubescent.

Inflorescence description:

*Flower arrangement and shape.*—Single, large, campanulate flowers in racemes turning upright to outward, basipetal flowering habit.

*Natural flowering season.*—June to July. Season can be extended by long day treatments.

*Time to flower.*—About 8 weeks after planting of rooted cutting.

*Flower longevity.*—On the plant, flowers last about 6 to 10 days; however, longevity of individual flowers is highly dependent on temperature and light conditions. Flowers persistent.

*Fragrance.*—Slight perfume scent.

*Inflorescence size.*—Height: 6 cm to 8 cm. Diameter: 5 cm to 7 cm.

*Number of flowers per inflorescence.*—2 to 4.

*Number of flowers per lateral stem.*—1 to 3.

*Number of flowers and buds per plant.*—About 20 to 50.

*Buds.*—Length: Up to 20 mm. Diameter: Up to 10 mm. Shape: Oblong, petals forming a ribbed tube. Rate of opening: 1 to 3 per day. Color: RHS 144D yellow-green.

*Flowers.*—Height: About 35 to 40 mm. Diameter: About 35 to 40 mm.

*Petals.*—Arrangement: Single, sympetalous, slightly corrugated, basally fused campanulate; persistent. Quantity per flower: 5. Length: Lobes about 12-14 mm. Width: About 15 mm to 17 mm. Overall Shape: Sympetalous with acute lobes. Tip: Acute. Base: Fused. Margin: Entire. Texture: Inside; silky with thin soft white hairs. Outside; shiny.

*Color* (*when opening* & *when fully opened*).—Outside bell: tip RHS N828 violet. base RHS N82D violet. Grooved line from base to tip: RHS N82D violet. Inside bell: tip RHS N82A violet. base RHS N82D violet. Grooved line from base to tip: RHS N82D violet. Fading: Fades to violet RHS 183D greyed-purple later RHS 199D grey-brown.

*Sepals.*—Arrangement: Basally fused. Appearance: Pubescent, Quantity per flower: 5-6. Length: About 14 mm to 17 mm. Width: About 8 to 12 mm. Overall shape: Ovate. Tip: Acute. Base: Truncate. Margin: Crenate. Texture: Pubescent, short, soft white hairs. Color (immature): Upper and lower surfaces: Green, RHS 138A. Color (mature): Upper and lower surfaces: Green, RHS 138A.

*Peduncles.*—Length: About 5 mm to 8 mm. Diameter: 1-2 mm. Strength: Strong. Color: Green, RHS 138A.

Reproductive organs:

*Androecium.*—Stamen: Quantity: 5, fused until pollen has shed. Anther: Shape: Lanceolate. Twisting when withering. Length: About 10-12 mm (just before flowering opening). Color: Yellow-green RHS 145A (just before flowering opening) and greyed-orange RHS 164C (when withering). Pollen: Amount: Plenty. Color: Yellow 11B.

*Gynoecium.*—Pistil: Quantity: 1. Length: About 23 mm to 27 mm. Stigma: Shape: Fivepartite. Color: Yellow-green RHS 145A. Style: Length: About 20-23 mm. Color: Yellow-green RHS 145A. Ovary: Color: White, RHS 155A.

Seed/fruit: None observed.

Weather tolerance: Plants of the new *Campanula* have exhibited good tolerance to drought, rain and wind, with low temperature resistance to 0° C.

Disease/pest resistance: Not tested.

Disease/pest susceptibility: Not tested.

I claim:

1. A new and distinct cultivar of *Campanula* plant named 'PKMM03', as illustrated and described herein.

* * * * *